United States Patent
Cuezva Marcos

(10) Patent No.: US 7,608,403 B2
(45) Date of Patent: Oct. 27, 2009

(54) METHOD FOR CANCER DETECTION, PROGRESSION ANALYSIS AND MALIGN TUMOUR PROGNOSIS BASED ON THE STUDY OF METABOLIC MARKERS OF THE CELL

(75) Inventor: Jose Manuel Cuezva Marcos, Madrid (ES)

(73) Assignee: Universidad Autonoma de Madrid, Madrid (ES)

( * ) Notice: Subject to any disclaimer, the term of this patent is extended or adjusted under 35 U.S.C. 154(b) by 0 days.

(21) Appl. No.: 10/514,771

(22) PCT Filed: May 20, 2003

(86) PCT No.: PCT/ES03/00228

§ 371 (c)(1),
(2), (4) Date: Jun. 21, 2006

(87) PCT Pub. No.: WO03/100430

PCT Pub. Date: Dec. 4, 2003

(65) Prior Publication Data

US 2007/0003988 A1    Jan. 4, 2007

(30) Foreign Application Priority Data

May 24, 2002  (ES)  ............................. 200201190

(51) Int. Cl.
*G01N 33/53*    (2006.01)

(52) U.S. Cl. ...................................................... 435/7.1
(58) Field of Classification Search ................... 435/7.1
See application file for complete search history.

(56) References Cited

OTHER PUBLICATIONS

Klouwen and Appelman (Feb. 1967, Cancer Research, 27(1):255-260).*
Klouwen and Appelman (Cancer Research, Feb. 1967, 27(1):255-260).*
Moser et al (PNAS, Jun. 2001, 98(12):6656-6661).*
Appelman (Cancer Research, Feb. 1967, 27(1):255-260).*
Cuezva et al (Cancer Research, Nov. 2002, 62:6674-6681).*
Tockman et al (Cancer Res., 1992, 52:2711s-2718s).*

* cited by examiner

*Primary Examiner*—Sean E Aeder
(74) *Attorney, Agent, or Firm*—Fay Kaplun & Marcin, LLP

(57) ABSTRACT

Described is a method for cancer detection, progression analysis and malign tumor prognosis based on the study of metabolic markers of the cell. The method consists in using the study of the protein expression of the bioenergetic function of the mitochondrion, such as the beta-catalytic subunit of the H-ATP synthase, in relation to structural proteins and mitochondrial respiration, such as hsp 60 and cytochrome oxidase subunits I and IV respectively, and said mitochondrial bioenergetic index, (ratio of beta-ATPasa/hsp60; beta-ATPasa/COX I; beta-ATPasa/COX IV) which relates to the cellular protein expression of the glycolytic pathway, such as glyceraldehyde-3-phosphate dehydrogenase and pyruvate kinase M, in order to generate the bioenergetic index of the cell.

3 Claims, 4 Drawing Sheets

METHOD FOR CANCER DETECTION, PROGRESSION ANALYSIS AND MALIGN TUMOUR PROGNOSIS BASED ON THE STUDY OF METABOLIC MARKERS OF THE CELL

FIELD OF THE INVENTION

This invention has its application in the Medical and Veterinary Oncology, for detection and tracking of malign tumours, particularly inscribed in the field of Biotechnology. From a conceptual point of view, the catalytic subunit β of the mitochondrial complex of the H(+)-ATP synthase, as well as the bioenergetic mitochondrial index and the bioenergetic index of the cell, could also be of use in the fields of the Neurosciences and the Cardiovascular diseases, and in general in all those pathologies that deal with hypoxia and/or anoxia of tissues, as well as other pathologies associated to dysfunctions of the mitochondrial cell activity.

BACKGROUND OF THE INVENTION

The mitochondrion is the organule of the eukaryotic cell responsible for the energy supply. The enzymatic machinery responsible in the last step of the synthesis of the cellular ATP into the H(+)-ATP synthase, a rotary molecular engine that is located in the inner membrane of the mitochondrion [12]. In the last years, the mitochondrion has come to take an important role in studies related to Biomedicine due to its obvious implication in multiple manifestations of the human pathology. Specifically, in the case of cancer, because is the subcellular organule sensor and executor of the apoptosis program. The apoptosis is a genetic program of programmed cell death, that requires energy and is essential for the normal development of the organism. Alterations in the apoptosis program contribute to the progression of certain pathologies such as cancer and neurodegenerative diseases [10, 11].

The study of the energetic metabolism of cancer cells was a central issue in the cancer investigation until the beginning of 1970, decade in which was a relegated topic by the scientific community, due to the approach and development of the molecular biology of this disease. However, it was in 1930 when Otto Warburg formulated the hypothesis that tumour cells should have an altered mitochondrial function and this dysfunction had to explain the high aerobic glycolysis that characterize the majority of the tumour cells. While the glycolytic phenotype of many cancer cells and tumours have been demonstrated from the biochemical and molecular study, dysfunction of the mitochondrial function of the cancer cell was never established in the biology of cancer. In fact, we still are ignorant of the role that the mitochondrion plays in the neoplasic transformation, as well as in the support or promotion of the transformed state of the cell. Solely, and in the case of highly glycolytic rat hepatomas, his aberrant energetic metabolism has been explained by the decrease of the relative cell content of mitochondria [6]. In this concrete case, it has been described that the mitochondrial phenotype of the hepatomas is similar to the mitochondrial phenotype of the fetal liver, where an specific program of mitochondrial biogenesis limits the mitochondrial content of the cell [1].

On the other hand, it has recently been revealed that the execution of the apoptosis program requires the molecular components of the H(+)-ATP synthase of the mitochondrion [7, 8], as well as a functional oxidative phosphorylation in the cell [2, 4]. These results suggest that cells with a relatively low expression of H(+)-ATP synthase and/or with a deficient functionality of oxidative phosphorylation, of which is a bottleneck the same H(+)-ATP synthase, must be more resistant to the apoptosis, and therefore, should have favoured his clonal expansion in the context of the organism.

In the case of the present invention, there have been used monoclonal and polyclonal antibodies that specifically recognize mitochondrial proteins and proteins of the glycolytic pathway in "Western blot" and immunocytochemical techniques, with the aim to quantify the expression of these proteins in normal tissues and its corresponding tumours, to use them, alone in combination, as markers of the progression and prognosis of cancer.

In this way, it has been attained to show for the first time, that the catalytic subunit β of the mitochondrial complex of the H(+)-ATP synthase (β-F1-ATPase) has his expression decreased in liver, kidney and colon tumours, what implies to show that the mitochondrial function of the tumour cell is affected, confirming the hypothesis that Otto Warburg had stated in the beginning of the last century, and that had not been demonstrated in human carcinomas up to this moment. These results allow his extrapolation to mamma, lung, stomach, prostate and endometrium adenocarcinomas; to lung and larynx squamous carcinomas, as well as melanomas and lymphomas.

In liver carcinomas, the affection of the mitochondrial function is produced by repression of the mitochondrial biogenesis, as in a parallel way it is produced the lower expression of structural components of the mitochondrion, as are the marker Hsp 60 and the proper mitochondrial DNA (FIG. 1).

On the contrary, in kidney carcinomas (FIG. 2) and colon carcinomas (FIG. 3), the lower expression of the catalytic subunit β of the mitochondrial complex of the H(+)-ATP synthase is produced in absence of significative changes in the expression of Hsp 60, what indicates that in this type of carcinomas it is being affected the molecular mechanism that determines the grade of functional differentiation of the mitochondrion, that comes expressed by the ratio between the bioenergetic marker and the structural marker, that is, by the proportion β-F1-ATPase/Hsp 60. In mammal adenocarcinomas the lower expression of β-F1-ATPase is produced in a simultaneous way with a higher expression of Hsp 60 and cytochrome oxidase I, what means a very pronounced decrease of the proportion β-F1-ATPase/Hsp 60 and β-F1-ATPase/COX I in the tumour tissue.

In lung adenocarcinomas, the relative expression of β-F1-ATPase decreases very strongly with respect to the expression of the respiratory enzymes cytochrome oxidase I and IV (β-F1-ATPase/COX I and β-F1-ATPase/COX IV).

In lung squamous carcinomas, the relative expression of β-F1-ATPase decreases significantly with respect to the Hsp 60 expression (β-F1-ATPase/Hsp 60).

Moreover, we have shown that in a parallel manner that a decrease in the ratio β-F1-ATPase/Hsp 60, β-F1-ATPase/COX I and/or β-F1-ATPase/COX IV in cancer is produced, it is produced an increase in the expression of the glyceraldehyde-3-phosphate dehydrogenase (GAPDH) (FIGS. 2 and 3) and/or the pyruvate kinase isoform M (PK), markers of the glycolytic pathway.

Because of this reason, we define a bioenergetic index of the cell (BEC index) that relates the bioenergetic potentiality of the mitochondrion with the cellular glycolytic capacity, an index that expresses any of the proportions β-F1-ATPase/Hsp 60, β-F1-ATPase/COX I and/or β-F1-ATPase/COX IV with respect to the cellular expression of GAPDH (ratio β-F1-ATPase/Hsp 60/GAPDH, β-F1-ATPase/COX I/GAPDH, β-F1-ATPase/COX IV/GAPDH and/or PK (ratios β-F1-ATPase/Hsp 60/PK, β-F1-ATPase/COX I/PK, β-F1-ATPase/COX IV/PK). The BEC index also decreases in tumour cells with respect to the observed in healthy cells of the kidney (FIG. 2), colon (FIG. 3), mamma, stomach and lung.

Moreover, in the case of colon carcinomas, the β-F1-ATPase (FIG. 4) as well as the BEC index, are indicators of the patient survival.

BIBLIOGRAPHY

1. Cuezva J. M., Ostronoff L. K., Ricart J., Lopez de Heredia M., Di Llegro C. M., and Izquierdo J. M. Mitochondrial biogenesis in the liver during development and oncogenesis. J. Bioenerg. Biomembr. 29, 365-377 (1997).
2. Dey, R. and Moraes, C. T. Lack of Oxidative Phosphorylation and Low Mitochondrial Membrane Potential Decrease Susceptibility to Apoptosis and Do not Modulate the Protective Effect of Bcl-xL in Osteosarcoma Cells. J. Biol. Chem., 275:7087-7094 (2000)
3. Egea G., Izquierdo, J. M. Ricart, J. San Martin C. and Cuezva J. M. mRNA encoding the beta-subunit of the mitochondrial F1-ATPase complex is a localized mRNA in rat hepatocytes. Biochem. J. 322, 557-656 (1997).
4. Harris, M H, Vander Heiden, M G, Kron, S J, and Thompson, C B (2000) Role of oxidative phosphorylation in Bax toxicity. Mol. Cell. Biol. 20: 3590-3596.
5. Izquierdo J. M. and Cuezva J. M. Control of the translational efficiency of beta-F1-ATPase mRNA depends on the regulation of a protein that binds the 3'-untranslated region of the mRNA. Mol. Cell Biol. 17, 5255-5268 (1997).
6. Lopez de Heredia, J. M. Izquierdo, and J. M. Cuezva A Conserved Mechanism for Controlling the Translation of beta-F1-ATPase mRNA between the Fetal Liver and Cancer Cells J. Biol. Chem., Mar. 15, 2000; 275(10): 7430-7437.
7. Matsuyama S, Llopis J, Deveraux Q L, Tsien R Y, Reed J C. Changes in intramitochondrial and cytosolic pH: early events that modulate caspase activation during apoptosis. Nat Cell Biol. 2000, 2:318-25.
8. Matsuyama S, Xu Q, Velours J, Reed J C. The Mitochondrial F0F1-ATPase proton pump is required for function of the proapoptotic protein Bax in yeast and mammalian cells. Mol Cell. 1998 February; 1(3):327-36.
9. Ostronoff L K, Izquierdo J M, Enriquez J A, Montoya J, Cuezva J M. Transient activation of mitochondrial translation regulates the expression of the mitochondrial genome during mammalian mitochondrial differentiation. 1996. Biochem. J. 316:183-91.
10. Reed J C: Mechanisms of apoptosis avoidance in cancer. Curr. Opin. Oncol. 1999; 11:68-75.
11. Thompson C B. Apoptosis in the pathogenesis and treatment of disease. Science. 1995.267:1456-62.
12. Yoshida, M., Muneyuki, E. and Hisabori, T. ATP synthase—a marvellous rotary engine of the cell Nat. Rev. Mol. Cell Biol. 2 (9), 669-677 (2001)

DESCRIPTION OF THE INVENTION

The present invention that relates to a method for cancer detection, progression analysis and malign tumour prognosis based on the study of metabolic markers of the cell, whose purpose lies in being established as a procedure for cancer detection, analysis of tumour progression and its prognosis, based in the study of the functional capacity of the mitochondrion with respect to the glycolytic capacity of the cell.

The method for cancer detection, progression analysis and malign tumour prognosis based on the study of metabolic markers of the cell, is configured as a method for the detection of malignant tumours based in the determination of the relative expression of the catalytic subunit β of the mitochondrial complex of the H(+)-ATP synthase, as only marker or in combination with the mitochondrial markers Hsp 60, COX I and COX IV (proportions β-F1-ATPase/Hsp 60, β-F1-ATPase/COX I and/or β-F1-ATPase/COX IV), and this proportion is at the same time expressed with respect to the expression of a glycolytic marker (GAPDH, HK, PK) of the cell. The method that the invention proposes is configured in himself as an evident novelty in his specific field of application, as is the first time that is claimed and shown that the bioenergetic function of the mitochondrion brings a generic marker of cancer that we can call "bioenergetic sign or mark of cancer".

To specify, the method for the cancer detection, progression analysis and malign tumour prognosis based on the study of metabolic markers of the cell object of the invention, is created starting from the previous study of hepatocarcinomas, hepatoblastomas and adenocarcinomas of human kidney, mamma, lung, stomach and colon by means of immunological techniques of Western blot and immunocytochemistry using specific antibodies against the proteins used as markers.

It must be point out that as controls, there have been used non-tumour samples of human liver, kidney, mamma, lung, stomach and colon coming from autopsies and/or biopsies or from the non-tumour part adjacent to the tumour.

DESCRIPTION OF THE DRAWINGS

To complete the description that is being made and with the aim to help for a better understanding of the characteristics of the invention, it is accompanied to the present descriptive memory, as an integral part thereof, a set of planes for illustrative and non-limitative purposes, where has been described the following.

PREFERRED EMBODIMENT OF THE INVENTION

Figure 1:
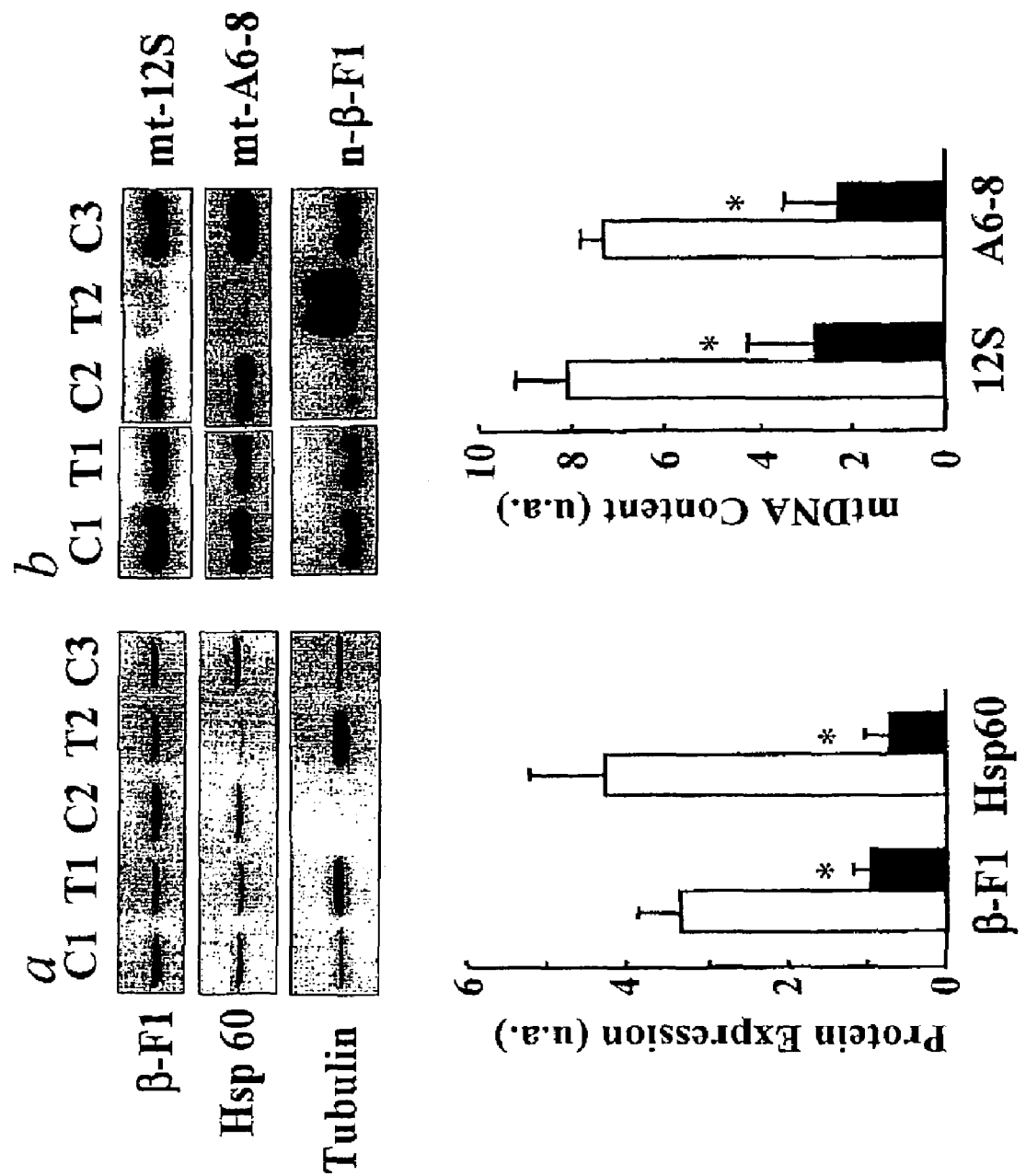
FIG. 1.—Represents the repression of the mitochondrial biogenesis in human hepatocarcinomas. a, Analysis of the expression of β-F1-ATPase (β-F1), Hsp 60 and tubulin in normal liver (C1-C3) and in hepatocarcinomas (T1-T2). The histogram shows the relative cell content of β-F1 and Hsp 60 with respect to the expression of tubulin in normal liver (white bars) and in hepatocarcinomas (black bars). b, Analysis of the mitochondrial DNA content (mtDNA) in normal liver (C1-C3) and in hepatocarcinomas (T1-T2). The histogram shows the relative cell content of the mitochondrial genes 12S and A6-8, with respect to the nuclear gen β-F1 in normal liver (white bars) and in hepatocarcinomas (black bars).
Figure 2:
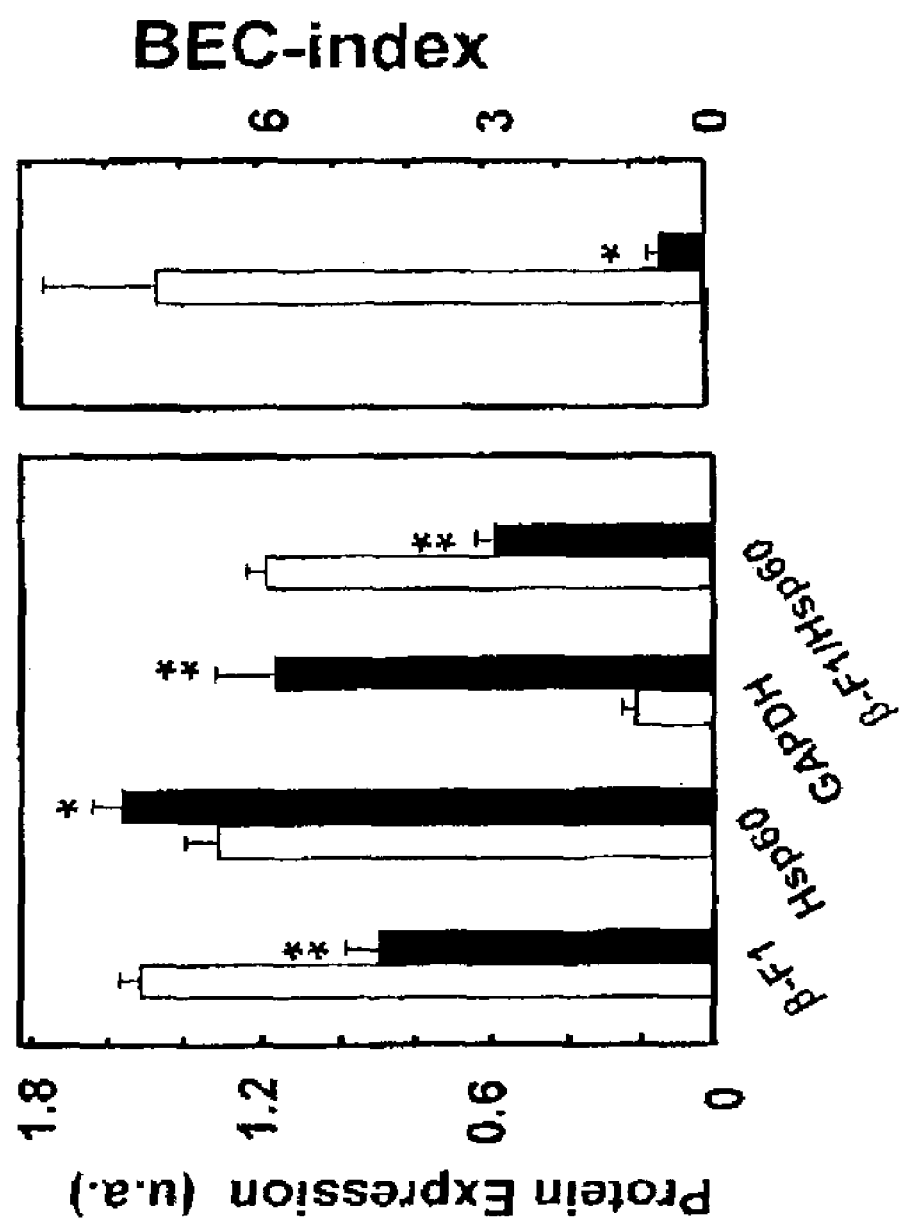
FIG. 2.—Corresponds to the analysis of the expression of β-F1-ATPase (β-F1), sp 60 and GAPDH, as well as to the bioenergetic index of the mitochondrion (β-F1/Hsp 60), and of the cell (BEC indexь β-F1/Hsp 60/GAPDH) in normal renal epithelium (white bars) and in kidney carcinomas (black bars).
Figure 3:
FIG. 3.—Shows the analysis of the bioenergetic index of the mitochondrion (β-F1/Hsp 60) and of the GAPDH expression, as well as of the bioenergetic index of the cell (BEC indexь β-F1/Hsp 60/GAPDH) in normal colon samples (white bars) and in colon carcinomas (black bars).
Figure 4:
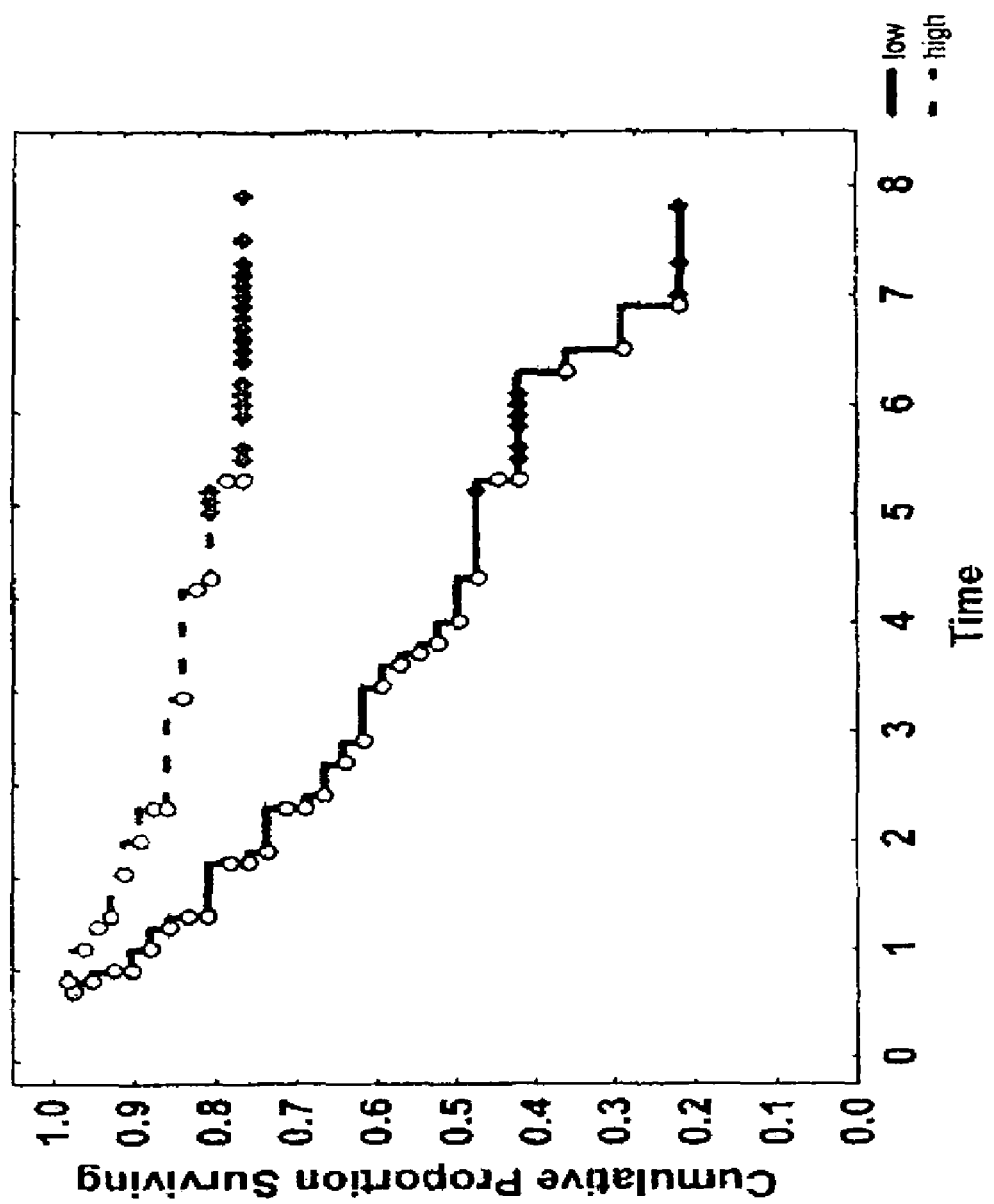
FIG. 4.—Shows finally the Kaplan-Meier analysis, where the β-F1-ATPase expression in colorectal carcinomas is correlated with the survival of patients. The broken line (in the upper part of the Figure), corresponds to tumours with a high level of expression of β-F1-ATPase. The solid line (in the lower part of the Figure) corresponds to tumours with a low level of expression of β-F1-ATPase.

The method for cancer detection, progression analysis and malign tumour prognosis based on the study of metabolic markers of the cell that is foreseen, consists of a method to determine the relative expression of β-F1-ATPase in the tumour cell to show his lower expression in cancer.

The analysis of the expression of Hsp 60, COX I and COX IV in the same sample and by means of the same technique, brings an inner control of the measurement system used, whether is by loading and/or by transference of the mitochondrial proteins to the membrane, at the same time allowing the calculus of the mitochondrial bioenergetic index (proportions β-F1-ATPase/Hsp 60, β-F1-ATPase/COX I, β-F1-ATPase/COX IV) of the sample.

The analysis of the expression of GAPDH and/or PK in the same sample and by means of the same technique, brings an inner control of the measurement system used, whether is by loading and/or by transference of the cell proteins to the membrane, at the same time allowing the calculus of the bioenergetic index of the cell (proportions β-F1-ATPase/COX I/GAPDH; β-F1-ATPase/COX IV/GAPDH; β-F1-ATPase/Hsp 60/PK; β-F1-ATPase/COX I/PK; β-F1-ATPase/COX IV/PK).

The hypothesis is that both the expression of β-F1-ATPase and the bioenergetic indexes of the mitochondrion and the cell (BEC index), are decreased in cancer, what affects negatively the apoptosis program, and permits the clonal expansion of the tumour cell. Although it is ignored exactly the mechanism thereby in cancer it is produced the inhibition of the β-F1-ATPase expression, this does not seem to be due to a lower expression of his mRNA, as the mRNA expression of β-F1-ATPase is increased in cancer. Possibly, the lower expression β-F1-ATPase in cancer is due to a control of the corresponding mRNA translation by the interaction of this with cell proteins.

The rabbit polyclonal antibody specific against the subunit β of the H(+)-ATP synthase of rat liver has been generated in the laboratory by several techniques. In one case, using as immunogen the purified protein of SDS polyacrylamide gel [3]. In another case, using as immunogen the protein synthesized in bacteria, by means of the cDNA expression of rat liver β-F1-ATPase [5], and later purification of the protein expressed through affinity techniques. The remaining antibodies that have been used have been commercial.

The expression of metabolic markers in tumours of liver, kidney, mamma, stomach, lung and colon, as well as the corresponding healthy tissues was made by Western blot and immunocytochemical techniques.

For the determination of markers by Western blot techniques 20 cuts of 17 micrometer thick of normal and tumour tissue of the same patient were extracted and processed, respectively, in 300 μl of a 50 mM Tris-HCl pH 8 buffer, that contains 150 mM Na Cl, 0.02% Sodium acide, 0.1% SDS, 1% Nonidet P-40, 0.5% sodium deoxycholate, 1 μg/μl aprotinin, 1 μg/μl antitrypsin, 0.4 mM EDTA, 10 mM NaF, and 0.75 mM PMSF at 4° C. for thirty minutes. After the extraction of the proteins, samples were centrifuged at 14,000 rpm at 4° C. for 25 minutes, and in the resulting supernatants the protein concentration was determined using the Bradford reactive. The fractionation of 15-30 μg of the proteins extracted from the normal and tumour tissue of the same patient was made in SDS gel 10% or 15% PAGE. Later on, the fractioned proteins in the gel were transferred to PVDF membranes for 1 hour at constant voltage. The immunological detection of the proteins was carried out using the following primary antibodies: anti-β-F1-ATPase (1:20,000), anti-Hsp 60 (1:2,000), anti-COX I (1:250), anti-COX IV (1:100) and anti-GAPDH (1:10,000), with the corresponding secondary antibody diluted in peroxidase conjugate at 1:3,000 and using the chemiluminescence method. The quantification of the intensity in the immunoreactivity signal of the different proteins was realized using an image digital analysis system.

For the determination of the expression in the protein markers by immunohistochemical techniques, sections of 4-5 μM thick corresponding to the samples of normal or pathological tissue, previously fixed in neutral formalin solution and paraffin-embedded, were incubated with the primary antibodies anti-β-F1-ATPase (1:3,000), anti-Hsp 60 (1:800) or anti-GAPDH (1:1,000). For the development of the different immunohistochemicals a detection method based in the diaminobenzidine was followed, using the Envision-Plus horseradish peroxidase system of DAKO Corporation. Afterwards, the cuts were stained with hematoxylin to highlight cells nuclei. The quantification of the chromogen intensity deposited in the cell was carried out by means of densitometric analysis of the chromogen intensity deposited per unit area of cytoplasm (30 μm$^2$) obtained starting from the digital magnified sample images (1,000×).

In the case of hepatocarcinomas and healthy liver there was also determined the relative cell content of mitochondrial DNA through western-blot techniques [9]. For this purpose, the cellular DNA was extracted by phenol from the homogenized samples in buffer 10 mM Tris HCl pH 7.5 that contains 10 mM EDTA, 0.5% SDS and 0.8 μg/μl proteinase K. The DNA obtained was precipitated with 2.5 volumes ethanol and 0.1 volumes sodium acetate 3M. DNA was resuspended in medium 10 mM Tris HCl pH 8.0, that contains 100 mM NaCl and 0.1 μg/μl RNAse. After incubation of one hour at room temperature SDS is added to 0.5% final concentration and it is extracted with phenol-chloroform-isoamilic (25:24:1) and the precipitation of DNA with ethanol and sodium acetate is repeated. The DNA was directed with the restriction enzyme BamHI and was fractioned on 0.8% agarose gel. The DNA fragments were transferred to nitrocellulose membranes under vacuum conditions for 4 hours at partial pressure of 10 mm mercury. The DNA fragments are fixed to the membrane by incubation of the same at 80° C. for 2 hours. The membranes were incubated with DNA sondes marked with $^{32}$P for the nuclear gen of the β-F1-ATPase and the mitochondrial genes of the ATPase 6-8 and 12 S. The hybridization conditions were 5×Denhardt's solution, 50% formamide, 0.5% SDS, 6×SSC and 0.132 mg/ml of salmon semen DNA. The membranes were washed following the next protocol: 10 minutes with 6×SSC at room temperature, 10 minutes with 2×SDS containing 0.1 SDS at 65° C. and 10 minutes with 1×SSC containing 0.1 SDS at 65° C. The membranes thus washed were exposed to autoradiographic films at −70° C. and the intensity of the bars corresponding to the different genes were quantified by densitometry.

The analysis of the samples of hepatocarcinomas, hepatoblastomas and focal nodular hyperplasias by immunocytochemical techniques showed a very significant decrease of the β-F1-ATPase and Hsp 60 expressions when compared with the expression of these markers in normal liver. Particularly, the expression of these two markers in hepatocarcinomas was of 13% for β-F1-ATPase and 30% for Hsp 60 in relation to the expression observed in normal liver.

In the case of hepatocarcinomas, it was shown this decrease in the expression of both markers in relation to the tubulin expression by western-blot techniques. Furthermore, it was shown that in hepatocarcinomas the relative content of mitochondrial DNA is much lower than that of the healthy liver, approximately 2-3 less.

This set of results indicate that in liver cancer it is produced a repression of the mitochondrial biogenesis of the cell.

The analysis of the Hsp 60 expression in adenocarcinomas of kidney, stomach and colon did not show significant variations with regard to the respective non-tumour tissue. On the contrary, the β-F1-ATPase expression is intensely decreased in kidney, stomach and colon tumours. Particularly, in carcinomas of these three tissues the decrease in the β-F1-ATPase expression is a 50% of the one observed in the respective normal tissues.

In mammal adenocarcinomas, the β-F1-ATPase expression is 40% lower than this protein expression in normal mammal tissue. Simultaneously, in mammal adenocarcinomas it is observed that Hsp 60 and cytochrome oxidase expressions are 700% and 300% higher respectively, than the observed in the normal mammal tissue.

In lung adenocarcinomas, the relative expression of β-F1-ATPase is 50% lower than the observed in normal lung tissue. Moreover, in lung adenocarcinomas, the expression of β-F1-ATPase is very decreased with respect to the expression in the respiratory enzymes cytochrome oxidase I and IV, which presents levels of expression 300% higher than the observed in normal lung tissue. In lung squamous adenocarcinomas, the relative expression of β-F1-ATPase is very decreased with respect to the Hsp 60 expression, being the ratio β-F1-ATPase/Hsp 60 a 20% of the observed in normal lung tissue.

Consistent with a lower activity of the bioenergetic function of the mitochondrion in cancer, it was observed that the activity of the glyceraldehyde-3-phosphate dehydrogenase (GAPDH) is strongly increased in tumours of kidney, mamma, lung and colon, finding a highly significant inverse relation between the bioenergetic index of the mitochondrion (ratio β-F1-ATPase/Hsp 60) and the glucolitic capacity of the cell, expressed these latter by the quantity of GAPDH. Then, it has been shown that GAPDH increases 600% in kidney tumours, 200% in colon tumours, 900% in mammal tumours and 400% in lung tumours, when compared with the GAPDH expression in their respective normal tissues. The PK expression in mammal and lung tumours is 500% and 250% higher, respectively, than the observed in normal mammal and lung tissue.

The BEC index (β-F1-ATPase/Hsp 60/GAPDH or β-F1-ATPase/Hsp 60/PK) for tumours of kidney, mamma, stomach, lung and colon is, therefore, much lower than in the respective healthy tissues. In this sense, the BEC index estimated by the ratio β-F1-ATPase/Hsp 60/GAPDH in kidney tumours is a 10% of the value found in normal kidney, in colon tumours is a 25% of the value found in normal colon, in stomach tumours is a 50% of the value found in normal stomach, in mammal adenocarcinomas is a 5% of the value found in normal mammal tissue, in lung adenocarcinomas is a 20% of the value found in normal lung and in lung squamous carcinomas is a 10% of the value found in normal lung. The BEC index estimated by the ratio β-F1-ATPase/Hsp 60/PK in stomach adenocarcinomas is a 50% of the value found in normal stomach, in mammal adenocarcinomas is a 5% of the value found in normal mammal tissue, in lung adenocarcinomas is a 25% of the value found in normal lung and in lung squamous carcinomas is a 30% of the value found in normal lung.

The study of the expressions of β-F1-ATPase, Hsp 60 and GAPDH as well as the mitochondrial bioenergetic index (β-F1-ATPase/Hsp 60) and the cellular bioenergetic index (β-F1-ATPase/Hsp 60/GAPDH) in colorectal tumours for which there is known the survival of patients, shows the existence of a significant relation between the level of expression of the β-F1-ATPase and of the mitochondrial and cellular bioenergetic indexes with the survival and prognosis of patients.

The invention claimed is:

1. A method for cancer detection, cancer progression analysis and malign tumor progression in cancer cells, comprising the steps of:
   detecting the expression level of the polypeptide of subunit β of H(+)-ATP synthase of the cancer cells;
   calculating a ration of the expression of β-F1-ATPase to Hsp60 of the cancer cells; and
   comparing the ration with a ratio of β-F1-ATPase to Hsp60 of one of a) control non-cancerous cells of a same cellular type as the cancer cells and b) control cancer cells of a same cellular type as the cancer cells,
   wherein, if the ratio of the cancer cells is lower than the ratio of the control non-cancerous cells, a presence of cancer is indicated, and
   wherein, if the ratio of the cancer cells is lower than the ratio of the control cancer cells, that the cancer cells are further progressed cancer cells is implied and a subject from which the cancer cells were obtained has a worse prognosis than a subject from which the control cancer cells were obtained is implied.

2. The method according to claim 1, wherein the detecting step includes a use of immunological techniques.

3. The method according to claim 2, wherein the immunological techniques are immunological techniques selected from a group consisting of: a Western blot, an immunohistochemical technique, and an immunocytochemical technique.

* * * * *